United States Patent [19]

Skuballa et al.

[11] Patent Number: 4,789,685
[45] Date of Patent: Dec. 6, 1988

[54] 9-FLUOROPROSTAGLANDIN DERIVATIVES, THEIR PREPARATION AND USE AS MEDICINAL AGENTS

[75] Inventors: Werner Skuballa; Bernd Raduechel; Norbert Schwarz; Helmut Vorbrueggen; Walter Elger; Olaf Loge; Michael-Harold Town, all of Berlin, Fed. Rep. of Germany

[73] Assignee: Schering Aktiengesellschaft, Berlin and Bergkamen, Fed. Rep. of Germany

[21] Appl. No.: 4,733

[22] Filed: Jan. 20, 1987

Related U.S. Application Data

[60] Continuation of Ser. No. 615,427, May 30, 1984, abandoned, which is a division of Ser. No. 395,448, Sep. 6, 1982, abandoned.

[30] Foreign Application Priority Data

Jul. 3, 1981 [DE] Fed. Rep. of Germany ....... 3126924

[51] Int. Cl.$^4$ .................. C07C 177/00; A61K 31/557
[52] U.S. Cl. .................................. 514/530; 514/570; 514/573; 514/601; 514/616; 514/729; 560/62; 560/121; 562/472; 562/503; 561/98; 561/152; 568/838
[58] Field of Search ................. 560/121, 62; 562/503, 562/472; 568/838; 564/98, 152; 514/530, 573, 570, 601, 616, 729

[56] References Cited

FOREIGN PATENT DOCUMENTS 2628364 1/1977 Fed. Rep. of Germany ...... 560/121

OTHER PUBLICATIONS

Muchowski Chemistry, Biochemistry and Pharmacological Activity of Prostanoids, p. 51, (1978).
Nicolau et al., Prostaglandins, 31(4), p. 811 (1986).

Primary Examiner—Robert Gerstl
Attorney, Agent, or Firm—Millen & White

[57] ABSTRACT 9-fluoroprostane derivatives of Formula I

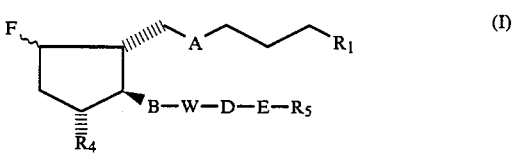

wherein
$R_1$ is $CH_2OH$ or

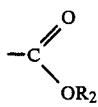

wherein $R_2$ is hydrogen, alkyl, cycloalkyl, aryl, or a heterocyclic residue; or $R_1$ is the residue

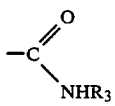

wherein $R_3$ is an acid residue or $R_2$ and
A is —$CH_2$—$CH_2$— or cis—CH=CH—,
B is —$CH_2$—$CH_2$—, trans—CH=CH— or —C≡C,
W is a free or functionally modified hydroxymethylene group wherein the OH-group can be in the α- or β- position,
D and E jointly are a direct bond or
D is straight-chain or branched alkylene or alkenylene of 1-10 carbon atoms which can optionally be substituted by fluorine atoms, and E is oxygen or sulfur, a direct bond, —C≡C— or —$CR_6$=$CR_7$— wherein $R_6$ and $R_7$ differ from each other and each is hydrogen, chlorine, or alkyl,
$R_4$ is a free or functionally modified hydroxy group, and
$R_5$ is hydrogen, an optionally substituted aliphatic group, e.g., alkyl or halosubstituted alkyl, cycloalkyl, optionally substituted aryl or a heterocyclic group, and, when $R_2$ is H, the physiologically compatible salts thereof with bases,
have valuable pharmacological properties, e.g., as luteolytics or abortifacients.

39 Claims, No Drawings

9-FLUOROPROSTAGLANDIN DERIVATIVES, THEIR PREPARATION AND USE AS MEDICINAL AGENTS

This is a continuation, of application Ser. No. 615,427, filed May 30, 1984 which is a div. of Ser. No. 395,448, filed July 6, 1982 now abandoned.

BACKGROUND OF THE INVENTION

The present invention relates to novel 9-fluoroprostaglandin derivatives, a process for their preparation and their use as medicinal agents.

It is known from the very voluminous state of the art of the prostaglandins and their analogs that this class of compounds, due to their biological and pharmacological properties, is suitable for the treatment of mammals, including man. Their use as medicines, however, frequently presents difficulties. Most of the natural prostaglandins have a period of efficacy too brief for therapeutic purposes, since they are metabolically broken down too rapidly by various enzymatic processes. All structural modifications aim at raising their duration of effectiveness as well as their selectivity of efficacy.

DOS No. 2,628,364 discloses prostane derivatives having a fluorine atom in the 9-position. The compounds of this laid-open application contain an alkyl group in the 15-position as the sole structural alteration in comparison with the natural side chains of the prostaglandins.

SUMMARY OF THE INVENTION

Accordingly, it is an object of this invention to provide new prostaglandin compounds having the desirable improved properties mentioned above.

Upon further study of the specification and appended claims, further objects and advantages of this invention will become apparent to those skilled in the art.

These objects have been achieved by providing 9-fluoroprostane derivatives of Formula I

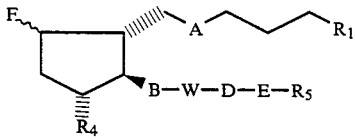

wherein
R$_1$ is CH$_2$OH or

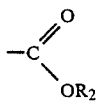

wherein R$_2$ is hydrogen, alkyl, cycloalkyl, aryl, or a heterocyclic residue; or R$_1$ is

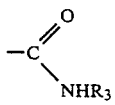

wherein R$_3$ is an acid residue or R$_2$;
A is —CH$_2$—CH$_2$— or cis—CH=CH—;
B is —CH$_2$—CH$_2$—, trans—CH=CH— or C≡C—;
W is a free or functionally modified hydroxymethylene group wherein the OH-group can be in the α- or β-position,
D and E jointly are a direct bond or
D is a straight chain or branched alkylene or alkenylene of 1-10 carbon atoms which can optionally be substituted by fluorine atoms.
E is oxygen, sulfur, a direct bond, —C≡C— or —CR$_6$=CR$_7$—, wherein R$_6$ and R$_7$ differ from each other and each is hydrogen, chlorine or alkyl;
R$_4$ is a free or functionally modified hydroxy group; and
R$_5$ is hydrogen, an optionally substituted aliphatic group, e.g., alkyl or halosubstituted alkyl, cycloalkyl, optionally substituted aryl or a heterocyclic group, and, when R$_2$ is hydrogen, the physiologically compatible salts thereof with bases.

It has been discovered that longer duration of effectiveness, greater selectivity, and improved efficacy can be attained by additional structural modifications in the lower side chain and/or in the 1-position of the 9-fluoroprostaglandins as described above.

DETAILED DISCUSSION

The flourine atom in the 9-position of Formula I can be in the α- or β-position.

Suitable alkyl groups R$_2$ can be linear or branched alkyl groups of 1-10 carbon atoms, e.g. methyl, ethyl, propyl, butyl, isobutyl, tert-butyl, pentyl, neopentyl, hexyl, heptyl, decyl, etc. The alkyl groups R$_2$ can optionally be mono- to polysubstituted by halogen atoms(F, Cl, Br), alkoxy groups, optionally substituted aryl or aroyl groups wherein the aryl portion and the substituents are as defined below for the corresponding R$_2$ groups per se, di-C$_{1-4}$-alkylamino, and tri-C$_{1-4}$-alkylammonium. Single substitution is preferred. Examples of such substituents include fluorine, chlorine, bromine, phenyl, dimethylamino, diethylamino, methoxy, ethoxy, etc. Preferred alkyl groups R$_2$ are those of 1-4 carbon atoms, such as, for example methyl, ethyl, propyl, dimethylaminopropyl, isobutyl or butyl.

Suitable aryl groups R$_2$ can be substituted or unsubstituted. Examples include phenyl, 1-naphthyl, and 2-naphthyl, each of which can be substituted by 1-3 halogen atoms, phenyl, 1-3 alkyl groups of 1-4 carbon atoms each, or a chloromethyl, fluoromethyl, trifluoromethyl, carboxy, hydroxy, or alkoxy group of 1-4 carbon atoms. Substitution in the 3- and 4-position on the phenyl ring is preferred, e.g. by fluorine, chlorine, alkoxy, or trifluoromethyl, or in the 4-position by hydroxy.

The cycloalkyl group R$_2$ can contain 3-10, preferably 5 or 6 carbon atoms in the ring. The rings can be substituted by alkyl groups of 1-4 carbon atoms. Examples include cyclopentyl, cyclohexyl, methylcyclohexyl, and adamantyl.

Suitable heterocyclic groups R$_2$ include 5- and 6-membered heterocycles, containing at least one hetero atom, preferably nitrogen, oxygen, or sulfur and preferably aromatic monocycles, the remaining atoms being carbon atoms. Examples include: 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, 2-tetrazolyl, and others.

Suitable acid residues R$_3$ are physiologically compatible acid residues which produce physiologically compatible compounds. Preferred acids are organic carboxylic acids and sulfonic acids of 1-15 carbon atoms pertaining to the aliphatic, cycloaliphatic, aromatic, aromatic-aliphatic, and heterocyclic series. The acids are usually hydrocarbons but the heterocyclic and other non-hydrocarbon acids are fully equivalent as are the substituted analogs of all of these. These acids can be saturated, unsaturated and/or polybasic and/or substituted in the usual way. Examples of substituents include alkyl, hydroxy, alkoxy, oxo, or amino groups or halogen atoms. The following carboxylic acids are recited as examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, ter-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-,di-, and trichloroacetic acids, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy, or carboxy groups, nicotinic acid, isonicotinic acid, furan-2-carboxylic acid, cyclopentylpropionic acid. Especially preferred acyl residues are those of up to 10 carbon atoms. Examples of suitable sulfonic acids include methanesulfonic acid, ethanesulfonic acid, isopropanesulfonic acid, $\beta$-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethyl-(or diethyl-)-aminosulfonic acid, N,N-bis ($\beta$-chloroethyl)aminosulfonic acid, N,N-diisobutylaminosulfonic acid, N,N-dibutylaminosulfonic acid, pyrrolidino-, piperidino-, piperazino-, N-methylpiperazino-, and morpholinosulfonic acids.

The hydroxy groups in W and $R_2$ can be functionally modified, for example by etherifying or esterifying them; the modified hydroxy group in W can likewise be in the $\alpha$- or $\beta$-position.

Suitable ether and acyl residues are well known to persons skilled in the art. Ether residues which can be readily split off are preferred and include, e.g. the tetrahydropyranyl, tetrahydrofuranyl, $\alpha$-ethoxyethyl, trimethylsilyl, dimethylsilyl, tert-butylsilyl, and tribenzylsilyl residues. The acyl residues are those doscribed for $R_3$, for example, particularly worth mentioning are acetyl, propionyl, butyryl, and benzoyl.

Aliphatic groups $R_5$ include straight-chain and branched saturated and unsaturated residues, e.g., alkyl or alkenyl, preferably saturated ones, of 1–10, especially 1–6 carbon atoms, which can optionally be substituted by optionally substituted aryl and by halo. The optionally substituted aryl groups are those described for $R_2$. Examples include methyl, ethyl, propyl, butyl, isobutyl, tert-butyl, pentyl, hexyl, heptyl, octyl, butenyl, isobutenyl, propenyl, pentenyl, benzyl, m- and p-chlorobenzyl etc. If $R_5$ is halosubstituted, e.g., halosubstituted alkyl, suitable halogens are fluorine, chlorine, and bromine. The usual number thereof is 1–3.

The cycloalkyl group $R_5$ can contain 3–10, preferably 3–6 carbon atoms in the ring. The rings can be substituted by alkyl groups of 1–4 carbon atoms. Examples include cyclopropyl, cyclobutyl, cyclopentyl, cyclohexyl, methylcyclohexyl, and adamantyl.

Examples of substituted or unsubstituted aryl groups $R_5$ are those discussed above for $R_2$. Examples include phenyl, 1-naphthyl, and 2-naphthyl, each of which can be substituted by 1–3 halogen atoms, a phenyl group, 1–3 alkyl groups of respectively 1–4 carbon atoms, a chloromethyl, fluoromethyl, trifluoromethyl, carboxy, alkoxy, or hydroxy. Substitution in the 3- and 4-position on the phenyl ring is preferred, for example by fluorine, chlorine, alkoxy, or trifluoromethyl, or in the 4-position by hydroxy.

Suitable heterocyclic groups $R_5$ are also those listed for $R_2$, e.g., 5- and 6-membered heterocycles containing at least one hetero atom, preferably nitrogen, oxygen, or sulfur and preferably aromatic monocycles, the remainder of the atoms being C- atoms. Examples include 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, and others.

Suitable groups D include straight-chain or branched, saturated or unsaturated alkylene or alkenylene residues, preferably saturated ones of 1–10, especially 1–5 carbon atoms, which can optionally be substituted by 1–2 fluorine atoms. Examples include: methylene, fluoromethylene, difluoromethylene, ethylene, 1,2-propylene, ethylethylene, trimethylene, tetramethylene, pentamethylene, 1,1-difluoroethylene, 1-fluoroethylene, 1-methyltetramethylene, 1-methyltrimethylene, 1-methylene-ethylene, 1-methylenetetramethylene, etc.

Suitable for salt formation are inorganic and organic bases, all of which are familiar to those skilled in the art for the preparation of physiologically compatible salts. Examples include alkali metal hydroxides, such as sodium and potassium hydroxide, alkaline earth metal hydroxides, such as calcium hydroxide, ammonia, amines, such as ethanolamine, diethanolamine, triethanolamine, N-methylglucamine, morpholine, tris(hydroxymethyl)methylamine, etc.

Suitable alkyl groups $R_6$ and $R_7$ include straight chain and branched, saturated alkyl residues of 1–6, especially 1–4 C-atoms, such as those mentioned for $R_2$.

The present invention furthermore relates to a process for the preparation of the 9-fluoroprostane derivatives of Formula I comprising conventionally reacting a compound of Formula II

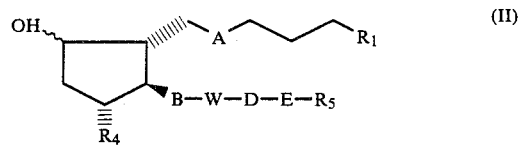 (II)

wherein
the OH-group can be in the $\alpha$- or $\beta$- position, $R_1$ is

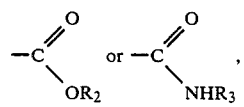

and A, $R_4$, W, B, D, E, and $R_5$ are as defined above, and free OH-groups in $R_4$ and W are blocked, to form an intermediary sulfonic acid ester and then reacting the latter, e.g., with a tetraalkylammonium fluoride; and, optionally, subsequently, in any desired sequence, liberating blocked hydroxy groups, and/or esterifying or etherifying blocked hydroxy groups and/or hydrogenating double bonds and/or saponifying an esterified carboxy group

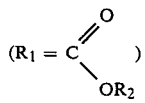

and/or esterifying a carboxy group ($R_2=H$) and/or converting a free carboxy group ($R_2=H$) into an amide

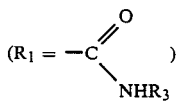

and/or reducing a free or esterfied carboxy group

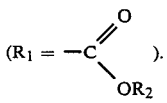

The reaction of the compounds of Formula II to obtain a sulfonic acid ester can be conducted conventionally with an alkyl- or arylsulfonyl chloride or an alkyl- or arylsulfonic acid anhydride in the presence of an amine, e.g. pyridine, 4-dimethylaminopyridine, or triethylamine at temperatures of $-60°$ C. to $+100°$ C., preferably $-20°$ C. to $+50°$ C. The nucleophilic substitution of the 9-sulfonate by a fluorine atom is accomplished with a tetraalkylammonium fluoride, preferably tetrabutylammonium fluoride, in an inert solvent, such as, for example, dimethylformamide, dimethyl sulfoxide, dimethylacetamide, dimethoxyethane, tetrahydrofuran, hexamethylphosphoric triamide, etc., at temperatures of $0°$ C. to $80°$ C., preferably $20°-45°$ C. Suitable alkyl or aryl groups in the sulfonyl chloride or sulfonic acid anhydride include those from p-toluene, methane, ethane, benzene, p-chloro-benzene, phenylmethane, isopropane, butane, isobutane.

If an alcohol of Formula II with a β-positioned 9-hydroxy group is employed in the intermediary sulfone ester formation and the subsequent nucleophilic substitution, then compounds of Formula I are produced having a 9α-positioned fluorine atom; if an alcohol with a α-positioned hydroxy group is used, compounds of Formula I are obtained having a 9β-positioned fluorine atom.

The conventional reduction to prepare compounds of Formula I with $R_1$ as $-CH_2OH-$ is carried out with a reducing agent suitable for the reduction of esters or carboxylic acids, such as, for example, lithium aluminum hydride, diisobutyl aluminum hydride, etc. Suitable solvents include diethyl ether, tetrahydrofuran, dimethoxyethane, toluene, etc. The reduction is conducted at temperatures from $-30°$ C. to the boiling temperature of the solvent employed, preferably at $0°-30°$ C.

The functionally modified hydroxy groups are also liberated by known methods. For example, hydroxy blocking groups, such as the tetrahydropyranyl residue, can be split off in an aqueous solution of an organic acid, e.g. oxalic acid, acetic acid, propionic acid, and others, or in an aqueous solution of an inorganic acid, e.g. hydrochloric acid. To improve solubility, a water-miscible, inert organic solvent is advantageously added. Suitable organic solvents include, for example, alcohols, such as methanol and ethanol, and ethers, such as dimethoxyethane, dioxane, and tetrahydrofuran. The preferred solvent is tetrahydrofuran. The splitting-off step is preferably effected at temperatures of $20°$ to $80°$ C.

The acyl groups are saponified for example, with alkali metal or alkaline earth metal carbonates or hydroxides, in an alcohol or in the aqueous solution of an alcohol. Suitable alcohols include aliphatic alcohols, such as, for example, methanol, ethanol, butanol, etc., preferably methanol. Typical alkali metal carbonates and hydroxides are potassium and sodium salts. The potassium salts are preferred.

Examples of suitable alkaline earth metal carbonates and hydroxides are calcium carbonate, calcium hydroxide, and barium carbonate. The reaction takes place at $-10°$ to $+70°$ C., preferably at $+25°$ C.

The ester group

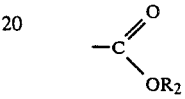

for $R_1$, wherein $R_2$ is an alkyl group of 1–10 carbon atoms, is introduced according to methods known to those skilled in the art. The 1-carboxy compounds can be reacted, for example, with diazo hydrocarbons in a manner known per se. Esterification with diazo hydrocarbons takes place, for example, by mixing a solution of the diazo hydrocarbon in an inert solvent, preferably in diethyl ether, with the 1-carboxy compound in the same or in another inert solvent, such as methylene chloride, for example. After the reaction has been completed in 1–30 minutes, the solvent is removed and the ester purified as usual. Diazoalkanes are either known or can be produced according to conventional methods [Org. Reactions 8: 389–394 (1954)].

The introduction of the ester group

for $R_1$, wherein $R_2$ is a substituted or unsubstituted aryl group, takes place by means of methods known to persons skilled in the art. For example, the 1-carboxy compounds can be reacted with the corresponding arylhydroxy compounds with dicyclohexylcarbodiimide in the presence of a suitable base, e.g. pyridine, DMAP [=dimethylaminopyridine], triethylamine, in an inert solvent. Solvents suitable for this purpose are methylene chloride, ethylene chloride, chloroform, ethyl acetate, tetrahydrofuran, preferably chloroform. The reaction is carried out at temperatures of between $-30°$ to $+50°$ C., preferably at $10°$ C.

The analogous compounds wherein $R_2$ is cycloalkyl or a heterocyclic residue are prepared analogously to the techniques mentioned above.

If any C═C-double bonds present in the primary product are to be reduced, the hydrogenation is conducted by conventional methods.

The 5,6-double bond can be conventionally hydrogenated at low temperatures, preferably at about $-20°$ C., in a hydrogen atmosphere in the presence of a noble metal catalyst. A suitable catalyst is, for example, 10% palladium on carbon.

If the 5,6- as well as the 13,14-double bonds are hydrogenated, the process is carried out at a higher temperature, preferably at about 20° C.

The prostaglandin derivatives of Formula I wherein $R_2$ is a hydrogen atom can be converted into a salt with suitable amounts of the corresponding inorganic bases, under conventional neutralization conditions. For example, the solid inorganic salt is obtained when dissolving the corresponding PG acids in water containing the stoichiometric quantity of the base, after evaporation of the water or after adding a water-miscible solvent, e.g. alcohol or acetone.

For the production of an amine salt, which also takes place in the usual conventional way, the PG acid is dissolved, for example, in a suitable solvent, e.g. ethanol, acetone, diethyl ether, acetonitrile, or benzene, and at least the stoichiometric amount of the amine is added to this solution. In this process, the salt is ordinarily obtained in the solid form or is conventionally isolated after evaporation of the solvent.

The introduction of the amide group

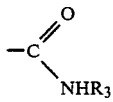

for $R_1$ takes place by using methids known to those skilled in the art. The carboxylic acids of Formula I ($R_2$=H) are first converted into the mixed anhydride in the presence of a tertiary amine, e.g. triethylamine, with isobutyl chloroformate. The mixed anhydride is reacted with the alkali metal salt of the corresponding amide or with ammonia ($R_3$=H) in an inert solvent or solvent mixture, such as, for example, tetrahydrofuran, dimethoxyethane, dimethylformamide, hexamethylphosphoric triamide, at temperatures of −30° to +60° C., preferably at 0°-30° C.

Another method for introducing the amide group

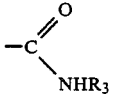

for $R_1$ resides in reacting a 1-carboxylic acid of Formula I ($R_2$=H), wherein free hydroxy groups are optionally blocked intermediarily, with compounds of Formula III $$O=C=N-R_3 \qquad (III)$$

wherein $R_3$ has the meanings given above.

The reaction of the compound of Formula I ($R_2$=H) with an isocyanate of Formula III likewise takes place with the addition of a tertiary amine, e.g. triethylamine or pyridine. The reaction can be conducted without a solvent or in an inert solvent, preferably acetonitrile, tetrahydrofuran, acetone, dimethylacetamide, methylene chloride, diethyl ether, toluene, etc. at temperatures of −80° to 100° C., preferably at 0°-30° C.

If the starting compound contains OH-groups in the prostane residue, these OH-groups also react. If, in the final analysis, end products are desired which contain free hydroxy groups in the prostane residue, it is advantageous to start with compounds wherein these groups are intermediarily blocked by ether or acyl residues which preferably can be readily split off.

The compounds of Formula II serving as the starting material are all well known or can be prepared from known starting materials, for example, by conventionally reducing a ketone of Formula IV

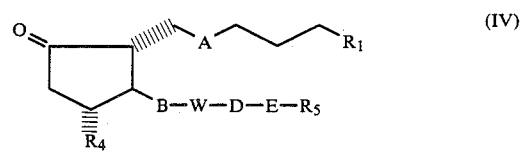

wherein
$R_1$ is

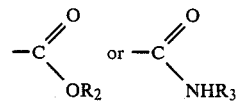

and

A, B, W, D, E, and $R_5$ are as defined above, and free OH-groups in $R_4$ and W are blocked,
with sodium borohydride, lithium tris(tert-butoxy) aluminum hydride, etc., and, optionally, subsequently, conventionally separating the epimeric 9α- and 9β-positioned hydroxy compounds of Formula II.

The compound of Formula IV are all well known or conventionally prepared from known starting materials.

As compared with PGE derivatives, the novel 9-fluoroprostaglandins of this invention are distinguished by higher stability.

The novel-9-fluoroprostane derivatives of Formula I are valuable pharmaceuticals for administration to mammals including humans since they exhibit, with a similar spectrum of activity, a substantially improved higher specificity and, above all, considerably longer efficacy than the corresponding natural prostaglandins.

The novel prostaglandin analogs act strongly luteolytically, i.e. to trigger luteolysis, substantially smaller doses are required than in case of the corresponding natural prostaglandins.

Also for triggering abortions, especially upon oral or intravaginal administration, considerably lesser quantities of the novel prostaglandin analogs are necessary as compared with the natural prostaglandins.

When recording the isotonic uterine contraction on anesthetized rats and on the isolated rat uterus, it is found that the compounds of this invention are substantially more efficacious and that their effects are of a longer duration than in case of the natural prostaglandins.

The novel prostaglandin derivatives are suitable, after a single enteral or parenteral administration, for inducing menstruation or interrupting pregnancy. They are furthermore suitable for synchronizing the sexual cycle in female mammals, such as rabbits, cattle, horses, pigs, etc. Furthermore, the prostaglandin derivatives of the present invention are suitable for cervix dilation as a preparation for diagnostic or therapeutic interventions.

The high tissue specificity of the compounds of this invention with antifertility activity is demonstrated in studies on other smooth-muscle organs, e.g. on the guinea pig ileum or on the isolated rabbit trachea, where a substantially lesser stimulation can be observed than caused by the natural prostaglandins. The compounds of this invention also have a bronchospasmolytic activity. Besides, they reduce swelling of the nasal mucous membrane.

The active agents of this invention inhibit gastric acid secretion, show a cytoprotective and ulcer-healing effect, and thus counteract the undesirable consequences of nonsteroidal anti-inflammatory agents (prostaglandin systhesis-inhibitors). They also have cytoprotective effects on the liver as well as the pancreas.

Several of the compounds show blood-pressure-lowering effects, a regulating effect on cardiac arrhythmias, and an inhibitory effect on platelet aggregation, with the ensuing conventional usage possibilities. Especially compounds with the structural features 16-aryloxy, 16-methyl or 16,16-dimethyl show the mentioned effects.

The novel prostaglandins can also be used in combination, for example, with β-blockers and diuretics.

For medical use, the active agents can be fully conventionally converted into a form suitable for inhalant, oral, parenteral, or local (e.g. vaginal) administration. Aerosol solutions are suitably prepared for inhalation purposes. Tablets, dragees, or capsules are suitable for oral administration, for example. Sterile, injectable aqueous or oily solutions are utilized for parenteral administration. Suppositories are suitable and customary, for example, for vaginal administration.

Consequently, the invention also concerns medicinal agents containing the compounds of Formula I and customary auxiliary agents and excipients.

The pharmacologically active compounds of this invention can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The dosage of the compounds according to this invention is usually 1–1500 μg/kg/day when administered to human patients as drugs for the treatment of the mentioned diseases.

The active agents of this invention are to be utilized, in conjunction with the auxiliary compounds known and customary in galenic pharmacy, for example to produce preparations for triggering abortion, for cycle regulation, for induction of labor, or for the treatment of hypertonia. For this purpose, and also for the other applications, the preparations can contain 0.01–50 mg of the active compound.

Without further elaboration, it is believed that one skilled in the art can, using the preceding description, utilize the present invention to its fullest extent. The following preferred specific embodiments are, therefore, to be construed as merely illustrative, and not limitative of the remainder of the dsclosure in any way whatsoever. In the following examples, all temperatures are set forth uncorrected in degrees Celsius; unless otherwise indicated, all parts and percentages are by weight.

EXAMPLE 1

(5Z,13E)-(9R,11R,15R)-11,15-Dihydroxy-9-fluoro-16-phenoxy-17,18,19,20-tetranor-5,13-prostadienoic Acid Methyl Ester At 0° C., 3.8 g of p-toluenesulfonic acid chloride is added to a solution of 5.7 g of (5Z,13E)-(9S,11R,15R)-9-hydroxy-11,15-bis(tetrahydropyran-2-yloxy)-16-phenoxy-17,18,19,20-tetranor-5,13-prostadienoic acid methyl ester (prepared from the corresponding acid in methylene chloride with ethereal /0.5-molar diazomethane solution at 0° C.) in 18 ml of pyridine; the mixture is stirred for 16 hours at ice bath temperature and 48 hours at room temperature. Then the mixture is combined with 15 ml of water, agitated for 3 hours at 20° C., diluted with ether, shaken in succession with water, 5% sulfuric acid, 5% sodium bicarbonate solution, and water, dried over magnesium sulfate, and evaporated under vacuum. Chromatography of the residue on silica gel yields with hexane/ethyl acetate (3+2) 5.2 g of the 9-tosylate as a colorless oil.

IR: 2950, 2875, 1733, 1600, 1590, 1496, 1365, 1240, 974 cm$^{-1}$.

13 g of tetrabutylammonium fluoride (dried by repeated concentration with toluene) is added to a solution of 5.2 g of the above-produced 9-tosylate in 75 ml of absolute dimethyl sulfoxide, and the solution is stirred for 1.5 hours at 22° C. under argon. The mixture is then diluted with ether, shaken four times with water, dried over magnesium sulfate, and evaporated under vacuum. The residue is purified by chromatography on silica gel. With hexane/ethyl acetate (9+1) as the eluent, the corresponding $\Delta^{8,9}$-compound is first obtained and then, as the more polar component, 0.72 g of (5Z,13E)-(9R,11R,15R)-11,15-bis(tetrahydropyran-2-yloxy)-9-fluoro-16-phenoxy-17,18,19,20-tetranor-5,13-prostadienoic acid methyl ester as a colorless oil.

IR: 2955, 1733, 1600, 1588, 1495, 970 cm$^{-1}$.

To split off blocking groups, 0.72 g of the above-produced 9β-fluorine compound is agitated for 16 hours at 22° C. with 20 ml of a mixture of acetic acid, water, and tetrahydrofuran (65+35+10) and then evaporated under vacuum. The residue is purified by chromatography on silica gel. With ether as the eluent, 370 mg of the title compound is obtained as a colorless oil.

IR: 3600, 3430 (broad), 2952, 2930, 2870, 1730, 1600, 1588, 1495, 970 cm$^{-1}$.

EXAMPLE 2

(5Z,13E)-(9S,11R,15R)-11,15-Dihydroxy-9-fluoro-16-phenoxy-17,18,19,20-tetranor-5,13-prostadienoic Acid Methyl Ester At 20° C., 3.4 g of p-toluenesulfonic acid chloride is added to a solution of 4.8 g of (5Z,13E)-(9R,11R,15R)-9-hydroxy-11,15-bis(tetrahydropyran-2-yloxy)-16-phenoxy-17,18,19,20-tetranor-5,13-prostadienoic acid methyl ester (prepared from the corresponding acid in methylene chloride with 0.5-molar ethereal diazomethane solution at 0° C.) in 27 ml of pyridine; the mixture is stirred for 20 hours at 20° C. The mixture is then combined with 12 ml of water, agitated for 3 hours at 20° C., diluted with ether, shaken in succession with water, 5% sulfuric acid, 5% sodium bicarbonate solution, and water, dried over magnesium sulfate, and evaporated under vacuum, thus obtaining 6.05 g of the 9-tosylate as a colorless oil.

IR: 2950, 2873, 1730, 1599, 1588, 1495, 1360, 972 cm$^{-1}$.

13.3 g of tetrabutylammonium fluoride (dried by repeated concentration with toluene) is added to a solution of 6.05 g of the above-produced 9-tosylate in 180 ml of absolute tetrahydrofuran, and the solution is refluxed for one hour under argon. Then the mixture is diluted with ether, shaken four times with water, dried over magnesium sulfate, and evaporated under vacuum. The residue is purified by chromatography on silica gel. With hexane/ether (7+3), 2.2 g of (5Z,13E)-(9S,11R,15R)-11,15-bis(tetrahydropyran-2-yloxy)-9-fluoro-16-phenoxy-17,18,19,20-tetranor-5,13-prostadienoic acid methyl ester is obtained as a colorless oil.

IR: 2956, 1731, 1599, 1588, 1495, 972 cm$^{-1}$.

To split off blocking groups, 2.2 g of the above-produced 9β-fluorine compound is stirred with 90 ml of a mixture of acetic acid/water/tetrahydrofuran (65+35+10) for 16 hours at 20° C. and then evaporated under vacuum. The residue is purified by chromatography on silica gel. Using ether as the eluent, 1.45 g of the title compound is obtaindd as a colorless oil.

IR: 3600, 3420 (broad), 2930, 2860, 1730, 1600, 1589, 1434, 970 cm$^{-1}$.

EXAMPLE 3

(13E)-(9R,11R,15R)-11,15-Dihydroxy-9-fluoro-16-phenoxy-17,18,19,20-tetranor-13-prostenoic Acid Methyl Ester Analogously to Example 1, 2.5 g of (13E)-(9S,11R,15R)-9-hydroxy-11,15-bis(tetrahydropyran-2-yloxy)-16-phenoxy-17,18,19,20-tetranor-13-prostenoic acid methyl ester yields 0.39 g of (13E)-(9R,11R,15R)-11,15-bis(tetrahydropyran-2-yloxy)-9-fluoro-16-phenoxy-17,18,19,20-tetranor-13-prostenoic acid methyl ester as a colorless oil.

IR: 2956, 1732, 1600, 1588, 1495, 970 cm$^{-1}$.

After splitting off the blocking groups according to Example 1, 0.24 g of the title compound is produced as a colorless oil.

IR: 3600, 3440 (broad), 2953, 2930, 2870, 1730, 1600, 1588, 1495, 970 cm$^{-1}$.

EXAMPLE 4

(13E)-(9S,11R,15R)-11,15-Dihydroxy-9-fluoro-16-phenoxy-17,18,19,20-tetranor-13-prostenoic Acid Methyl Ester In analogy to Example 2, 2.1 g of (13E)-(9R,11R,15R)-9-hydroxy-11,15-bis(tetrahydropyran-2-yloxy)-16-phenoxy-17,18,19,20-tetranor-13-prostenoic acid methyl ester yields 0.9 g of (13E)-(9S,11R,15R)-11,15-bis(tetrahydropyran-2-yloxy)-9-fluoro-16-phenoxy-17,18,19,20-tetranor-13-prostenoic acid methyl ester as a colorless oil.

IR: 2955, 1732, 1599, 1588, 1495, 971 cm$^{-1}$.

After splitting off the blocking groups according to Example 1, 0.52 g of the title compound is obtained as a colorless oil.

IR: 3600, 3450 (broad), 2930, 2860, 1731, 1600, 1589, 1494, 970 cm$^{-1}$.

EXAMPLE 5

(5Z,13E)-(9R,11R,15R)-11,15-Dihydroxy-16,16-dimethyl-9-fluoro-5,13-prostadienoic Acid Methyl Ester Analogously to Example 1, 2.9 g of (5Z,13E)-(9S,11R,15R)-11,15-bis(tetrahydropyran-2-yloxy)-16,16-dimethyl-9-hydroxy-5,13-prostadienoic acid methyl ester yields 0.35 g of (5Z,13E)-(9R,11R,15R)-11,15-bis(tetrahydropyran-2-yloxy)-16,16-dimethyl-9-fluoro-5,13-prostadienoic acid methyl ester as a colorless oil.

IR: 2960, 2855, 1732, 974 cm$^{-1}$.

EXAMPLE 6

(5Z,13E)-(9S,11R,15R)-11,15-Dihydroxy-16,16-dimethyl-9-fluoro-5,13-prostadienoic Acid Methyl Ester In analogy to Example 2, 1 g of (5Z,13E)-(9R,11R,15R)-9-hydroxy-11,15-bis(tetrahydropyran-2-yloxy)-16,16-dimethyl-5,13-prostadienoic acid methyl ester produces 0.44 g of (5Z,13E)-(9S,11R,15R)-11,15-bis(tetrahydropyran-2-yloxy)-16,16-dimethyl-9-fluoro-5,13-prostadienoic acid methyl ester as an oil.

IR: 2960, 2856, 1731, 974 cm$^{-1}$.

After splitting off the blocking groups as described in Example 2, 0.28 g of the title compound is obtained as an oil.

IR: 3600, 3440 (broad), 2935, 2860, 1732, 974 cm$^{-1}$.

The starting material for the above title compound is prepared as follows:

(6a)

(5Z,13E)-(9R,11R,15R)-9-Hydroxy-11,15-bis(tetrahydropyran-2-yloxy)-16,16-dimethyl-5,13-prostadienoic Acid Methyl Ester At 0° C., 6.5 g of sodium borohydride is added to a solution of 18 g of (5Z,13E)-(11R,15R)-11,15-bis(tetrahydropyran-2-yloxy)-16,16-dimethyl-9-oxo-5,13-prostadienoic acid methyl ester in 400 ml of methanol, and the mixture is stirred for 30 minutes at 0° C. Thereafter the mixture is diluted with ether, shaken four times with water, dried over magnesium sulfate, and evaporated under vacuum. The residue is purified by column chromatography on silica gel. With ether/hexane (4+1) as the eluent, 6.8 g of the corresponding 9α-hydroxy compound is first obtained and then, as the more polar component, 6.05 g of the title compound is produced as a colorless oil.

IR: 3600, 3420 (broad), 2960, 2855, 1731, 972 cm$^{-1}$.

EXAMPLE 7

(13E)-(9R,11R,15R)-11,15-Dihydroxy-16,16-dimethyl-9-fluoro-13-prostenoic Acid Methyl Ester Analogously to Example 1, 1.5 g of (13E)-(9S,11R,15R)-11,15-bis(tetrahydropyran-2-yloxy)-

16,16-dimethyl-9-hydroxy-13-prostenoic acid methyl ester yields 180 mg of (13E)-(9R,11R,15R)-11,15-bis(tetrahydropyran-2-yloxy)-16,16-dimethyl-9-fluoro-13-prostenoic acid methyl ester as an oil IR: 2962, 2855, 1731, 972 cm$^{-1}$.

After splitting off the blocking groups according to Example 1, 105 mg of the title compound is obtained as a colorless oil.

IR: 3600, 3440 (broad), 2935, 2860, 1731, 972 cm$^{-1}$.

EXAMPLE 8

(5Z,13E)-(9R,11R,16RS)-11,15α-Dihydroxy-9-fluoro-16-methyl-5,13-prostadienoic Acid Methyl Ester In analogy to Example 1, 3 g of (5Z,13E)-(9S,11R,16RS)-11,15α-bis(tetrahydropyran-2-yloxy)-9-hydroxy-16-methyl-5,13-prostadienoic acid methyl ester yields 0.33 g of (5Z,13E)-(9R,11R,16RS)-11,15α-bis(tetrahydropyran-2-yloxy)-9-fluoro-16-methyl-5,13-prostadienoic acid methyl ester as a colorless oil.

IR: 2965, 2855, 1732, 970 cm$^{-1}$.

After splitting off the blocking groups as disclosed in Example 1, 0.2 g of the title compound is obtained as an oil.

IR: 3600, 3430 (broad), 2935, 2860, 1732, 970 cm$^{-1}$.

EXAMPLE 9

(5Z,13E)-(9S,11R,16RS)-11,15α-Dihydroxy-9-fluoro-16-methyl-5,13-prostadienoic Acid Methyl Ester Analogously to Example 2, 1.3 g of (5Z,13E)-(9R,11R,16RS)-11,15α-bis(tetrahydropyran-2-yloxy)-9-hydroxy-16-methyl-5,13-prostadienoic acid methyl ester yields 0.58 g of (5Z,13E)-(9S,11R,16RS)-11,15α-bis(tetrahydropyran-2-yloxy)-9-fluoro-16-methyl-5,13-prostadienoic acid methyl ester as a colorless oil.

IR: 2966, 2858, 1732, 971 cm$^{-1}$.

After splitting off the blocking groups according to Example 2, 0.45 g of the title compound is produced as an oil.

IR: 3600, 3440 (broad), 2935, 2860, 1732, 971 cm$^{-1}$.

The starting material for the above title compound is prepared as follows:

(9a)

(5Z,13E)-(9R,11R,16RS)-11,15α-Bis(tetrahydro-pyran-2-yloxy)-9-hydroxy-16-methyl-5,13-prostadienoic Acid Methyl Ester Analogously to Example 6a, 7 g of (5Z,13E)(11R,16RS)-11,15α-bis(tetrahydropyran-2-yloxy)-16-methyl-9-oxo-5,13-prostadienoic acid methyl ester yields 2.4 g of the title compound as an oil.

IR: 3610, 3440 (broad), 2960, 2856, 1732, 971 cm$^{-1}$.

EXAMPLE 10

(5Z,13E)-(9R,11R,15R,16RS)-11,15-Dihydroxy-9,16-difluoro-5,13-prostadienoic Acid Methyl Ester In analogy to Example 1, 4.2 g of (5Z,13E)-(9S,11R,R,-15R,16RS)-11,15-bis(tetrahydropyran-2-yloxy)-9-hydroxy-16-fluoro-5,13-prostadienoic acid methyl ester produces 490 mg of (5Z,13E)-(9S,11R,15R,16RS)-11,15-bis(tetrahydropyran-2-yloxy)-9,16-difluoro-5,13-prostadienoic acid methyl ester as an oil.

IR: 2960, 1735, 976 cm$^{-1}$.

After splitting off the blocking groups as set forth in Example 1, 285 mg of the title compound is obtained as an oil. IR: 3600, 3430 (broad), 2930, 2857, 1734, 976 cm$^{-1}$.

EXAMPLE 11

(5Z,13E)-(9S,11R,15R,16RS)-11,15-Dihydroxy-9,16-difluoro-5,13-prostadienoic Acid Methyl Ester Analogously to Example 2, 0.8 g of (5Z,13E)-(9R,11R,15R,16RS)-11,15-bis(tetrahydropyran-2-yloxy)-9-hydroxy-16-fluoro-5,13-prostadienoic acid methyl ester (prepared from the corresponding 9-ketone according to Example 6a) yields 0.37 g of (5Z,13E)-(9S,11R,15R,16RS)-11,15-bis(tetrahydropyran-2-yloxy)-9,16-difluoro-5,13-prostadienoic acid methyl ester as a colorless oil.

IR: 2958, 1734, 974 cm$^{-1}$.

After the blocking groups have b.een split off as described in Example 2, 240 mg of the title compound is obtained as an oil.

IR: 3600, 3440 (broad), 2932, 2856, 1732, 974 cm$^{-1}$.

EXAMPLE 12

(5Z,13E)-(9R,11R,16RS)-11,15α-Dihydroxy-16,19-dimethyl-9-fluoro-5,13,18-prostatrienoic Acid Methyl Ester In analogy to Example 1, 2.8 g of (5Z,13E)-(9S,11R,16RS)-11,15α-bis(tetrahydropyran-2-yloxy)-16,19-dimethyl-9-hydroxy-5,13,18-prostatrienoic acid methyl ester yields 0.38 g of (5Z,13E)-(9R,11R,16RS)-11,15α-bis(tetrahydropyran-2-yloxy)-16,19-dimethyl-9-fluoro-5,13,18-prostatrienoic acid methyl ester as a colorless oil.

IR: 2960, 1731, 972 cm$^{-1}$.

After splitting off the blocking groups according to Example 1, 0.29 g of the title compound is obtained as an oil.

IR: 3600, 3440 (broad), 2935, 2855, 1731, 972 cm$^{-1}$.

EXAMPLE 13

(5Z,13E)-(9S,11R,16RS)-11,15α-Dihydroxy-16,19-dimethyl-9-fluoro-5,13,18-prostatrienoic Acid Methyl Ester In analogy to Example 2, 0.6 g of (5Z,13E)-((9R,11R,16RS)-11,15α-bis(tetrahydropyran-2-yloxy)-16,19-dimethyl-9-hydroxy-5,13,18-prostatrienoic acid methyl ester yields 0.24 g of (5Z,13E)-(9S,11R,16RS)-11,15α-bis(tetrahydropyran-2-yloxy)-16,19-dimethyl-9-fluoro-5,13,18-prostatrienoic acid methyl ester as a colorless oil.

IR: 2962, 1732, 970 cm$^{-1}$.

After the blocking groups have been split off as described in Example 1, 140 mg of the title compound is obtained as an oil.

IR: 3600, 3420 (broad), 2935, 2856, 1731, 970 cm$^{-1}$.

The starting material for the above title compound is produced as described below:

(13a)

(5Z,13E)-(9R,11R,16RS)-11,15α-Bis(tetrahydropyran-2-yloxy)-16,19-dimethyl-9-hydroxy-5,13,18-prostatrienoic Acid Methyl Ester In analogy to Example 6a, 4.2 g of (5Z,13E)-(11R,16RS)-11,15α-bis(tetrahydropyran-2-yloxy)-16,19-dimethyl-9-oxo-5,13,18-prostatrienoic acid methyl ester (prepared from the corresponding acid with ethereal diazomethane solution at 0° C.) yields 1.7 g of the title compound as a colorless oil.

IR: 3600, 3420 (broad), 2965, 2855, 1733, 970 cm$^{-1}$.

EXAMPLE 14

(13E)-(9R,11R,16RS)-11,15α-Dihydroxy-16,19-dimethyl-9-fluoro-13,18-prostadienoic Acid Methyl Ester Analogously to Example 1, 1.3 g of (13E)-(9S,11R,16RS)-11,15α-bis(tetrahydropyran-2-yloxy)-16,19-dimethyl-9-hydroxy-13,18-prostadienoic acid methyl ester yields 170 mg of (13E)-(9R,11R,16RS)-11,15α-bis(tetrahydropyran-2-yloxy)-16,19-dimethyl-9-fluoro-13,18-prostadienoic acid methyl ester as a colorless oil.

IR: 2962, 1730, 971 cm$^{-1}$.

After the blocking groups have been split off according to Example 1, 95 mg of the title compound is obtained as a colorless oil.

IR: 3610, 3450 (broad), 2937, 2855, 1730, 971 cm$^{-1}$.

EXAMPLE 15

(13E)-(9S,11R,16RS)-11,15α-Dihydroxy-16,19-dimethyl-9-fluoro-13,18-prostadienoic Acid Methyl Ester Analogously to Example 2, 0.9 g of (13E)-(9R,11R,16RS)-11,15α-bis(tetrahydropyran-2-yloxy)-16,19-dimethyl-9-hydroxy-13,18-prostadienoic acid methyl ester produces 0.38 g of (13E)-(9S,11R,16RS)-11,15α-bis(tetrahydropyran-2-yloxy)-16,19-dimethyl-9-fluoro-13,18-prostadienoic acid methyl ester as a colorless oil.

IR: 2960, 1731, 970 cm$^{-1}$.

After the blocking groups have been split off as described in Example 2, 220 mg of the title compound is obtained as a colorless oil.

IR: 3600, 3440 (broad), 2936, 2855, 1731, 970 cm$^{-1}$.

The starting material for the above title compound is produced as follows:

(15a)

(13E)-(9R,11R,16RS)-11,15α-Bis(tetrahydropyran-2-yloxy)-16,19-dimethyl-9-hydroxy-13,18-prostadienoic Acid Methyl Ester In analogy to Example 6a, 5.1 g of (13E)-(11R,16RS)-11,15α-bis(tetrahydropyran-2-yloxy)-16,19-dimethyl-9-oxo-13,18-prostadienoic acid methyl ester (prepared from the corresponding acid with ethereal diazomethane solution at 0° C.) yields 2.2 g of the title compound as a colorless oil.

IR: 3600, 3440 (broad), 2963, 2855, 1732, 970 cm$^{-1}$.

EXAMPLE 16

(5Z,13E)-(9R,11R,15R)-11,15-Dihydroxy-9-fluoro-16,16,19-trimethyl-5,13,18-prostatrienoic Acid Methyl Ester In analogy to Example 1, 2.9 g of (5Z,13E)-(9S,11R,15R)-11,15-bis(tetrahydropyran-2-yloxy)-9-hydroxy-16,16,19-trimethyl-5,13,18-prostatrienoic acid methyl ester yields 350 mg of (5Z,13E)-(9R,11R,15R)-11,15-bis(tetra-hydropyran-2-yloxy)-9-fluoro-16,16,19-trimethyl-5,13,18-prostatrienoic acid methyl ester as a colorless oil.

IR: 2960, 2855, 1732, 974 cm$^{-1}$.

After splitting off the blocking groups as described in Example 1, 190 mg of the title compound is obtained as an oil.

IR: 3600, 3440 (broad), 2942, 2850, 1732, 973 cm$^{-1}$.

EXAMPLE 17

(5Z,13E)-(9R,11R,15R)-11,15-Dihydroxy-9-fluoro-16-phenoxy-17,18,19,20-tetranor-5,13-prostadienoic Acid 350 mg of the methyl ester prepared as set forth in Example 1 is stirred for 5 hours with 10 ml of a solution made up of potassium hydroxide in ethanol and water (preparation: 2 g of potassium hydroxide is dissolved in 75 ml of ethanol and 25 ml of water). The mixture is then acidified with 10% citric acid solution to pH 4, extracted three times with methylene chloride, the organic extract is washed once with brine, dried over magnesium sulfate, and evaporated under vacuum. After chromatography of the residue on silica gel with methylene chloride/isopropanol (9+1) as the eluent, 300 mg of the title compound is obtained as a colorless oil.

IR: 3580, 3400 (broad), 2925, 2863, 1710, 1598, 1588, 1493, 970 cm$^{-1}$.

EXAMPLE 18

(5Z,13E)-(9S,11R,15R)-11,15-Dihydroxy-9-fluoro-16-phenoxy-17,18,19,20-tetranor-5,13-prostadienoic Acid In analogy to Example 17, 0.42 g of the methyl ester prepared according to Example 2 yields 0.34 g of the title compound as an oil.

IR: 3590, 3410 (broad), 2925, 2865, 1708, 1598, 1588, 1493, 970 cm$^{-1}$.

EXAMPLE 19

(13E)-(9R,11R,15R)-11,15-Dihydroxy-9-fluoro-16-phenoxy-17,18,19,20-tetranor-13-prostenoic Acid Analogously to Example 17, 0.26 g of the methyl ester produced in accordance with Example 3 yields 0.20 g of the title compound as colorless crystals (mp 98°–99° C.).

IR: 3600, 3400 (broad), 2924, 2864, 1709, 1599, 1588, 1493, 971 cm$^{-1}$.

EXAMPLE 20

(13E)-(9S,11R,15R)-11,15-Dihydroxy-9-fluoro-16-phenoxy-17,18,19,20-tetranor-13-prostenoic Acid In analogy to Example 17, 0.32 g of the methyl ester prepared by following Example 4 yields 0.26 g of the title compound as colorless crystals (mp 86°–87° C.).

IR: 3590, 3400 (broad), 2924, 2865, 1708, 1598, 1588, 1493, 970 cm$^{-1}$.

EXAMPLE 21

(5Z,13E)-(9R,11R,15R)-11,15-Dihydroxy-16,16-dimethyl-9-fluoro-5,13-prostadienoic Acid Analogously to Example 17, 0.15 g of the methyl ester produced according to Example 5 yields 0.11 g of the title compound as an oil. IR: 3600, 3405 (broad), 2952, 2860, 1710, 974 cm$^{-1}$.

EXAMPLE 22

(5Z,13E)-(9S,11R,15R)-11,15-Dihydroxy-16,16-dimethyl-9-fluoro-5,13-prostadienoic Acid Analogously to Example 17, 0.15 g of the methyl ester produced in accordance with Example 6 yields 0.10 g of the title compound as an oil.

IR: 3600, 3405 (broad), 2950, 2858, 1710, 975 cm$^{-1}$.

EXAMPLE 23

(13E)-(9R,11R,15R)-11,15-Dihydroxy-16,16-dimethyl-9-fluoro-13-prostenoic Acid

In analogy to Example 17, 0.2 g of the methyl ester prepared as in Example 7 yields 0.16 g of the title compound as an oil.

IR: 3600, 3410 (broad), 2952, 2862, 1708, 974 cm$^{-1}$.

EXAMPLE 24

(5Z,13E)-(9R,11R,16RS)-11,15α-Dihydroxy-9-fluoro-16-methyl-5,13-prostadienoic Acid In analogy to Example 17, 0.2 g of the methyl ester prepared according to Example 8 yields 0.16 g of the title compound as an oil.

IR: 3600, 3405 (broad), 2945, 2848, 1710, 976 cm$^{-1}$.

EXAMPLE 25

(5Z,13E)-(9S,11R,16RS)-11,15α-Dihydroxy-9-fluoro-16-methyl-5,13-prostadienoic Acid In analogy to Example 17, 0.2 g of the methyl ester prepared according to Example 9 yields 0.17 g of the title compound as an oil.

IR: 3600, 3405 (broad), 2950, 2852, 1710, 976 cm$^{-1}$.

EXAMPLE 26

(5Z,13E)-(9R,11R,15R,16RS)-11,15-Dihydroxy-9,16-difluoro-5,13-prostadienoic Acid Analogously to Example 17, 0.15 g of the methyl ester prepared as in Example 10 yields 0.12 g of the title compound as an oil.

IR: 3600, 3410 (broad), 2955, 2860, 1708, 976 cm$^{-1}$.

EXAMPLE 27

(5Z,13E)-(9S,11R,15R,16RS)-11,15-Dihydroxy-9,16-difluoro-5,13-prostadienoic Acid In analogy to Example 17, 0.15 g of the methyl ester prepared according to Example 11 yields 0.11 g of the title compound as an oil.

IR: 3600, 3405 (broad), 2954, 2858, 1708, 974 cm$^{-1}$.

EXAMPLE 28

(5Z,13E)-(9R,11R,16RS)-11,15α-Dihydroxy-16,19-dimethyl-9-fluoro-5,13,18-prostatrienoic Acid Analogously to Example 17, 0.30 g of the methyl ester produced according to Example 12 yields 0.26 g of the title compound as an oil.

IR: 3600, 3410 (broad), 2938, 2856, 1710, 976 cm$^{-1}$.

EXAMPLE 29

(5Z,13E)-(9S,11R,16RS)-11,15α-Dihydroxy-16,19-dimethyl-9-fluoro-5,13,18-prostatrienoic Acid In analogy to Example 17, 90 mg of the methyl ester produced by following Example 13 yields 75 mg of the title compound as an oil.

IR: 3600, 3410 (broad), 2940, 2856, 1710, 974 cm$^{-1}$.

EXAMPLE 30

(13E-(9R,11R,16RS)-11,15α-Dihydroxy-16,19-dimethyl-9-fluoro-13,18-prostadienoic Acid In analogy to Example 17, 80 mg of the methyl ester prepared according to Example 14 yields 50 mg of the title compound as an oil.

IR: 3600, 3405 (broad), 2952, 2840, 1710, 974 cm$^{-1}$.

EXAMPLE 31

(13E)-(9S,11R,16RS)-11,15α-Dihydroxy-16,19-dimethyl-9-fluoro-13,18-prostadienoic Acid Analogously to Example 17, 150 mg of the methyl ester obtained according to Example 15 yields 110 mg of the title compound as an oil.

IR: 3600, 3405 (broad), 2940, 2862, 1710, 974 cm$^{-1}$.

EXAMPLE 32

(5Z,13E)-(9R,11R,15R)-11,15-Dihydroxy-9-fluoro-16,16,19-trimethyl-5,13,18-prostatrienoic Acid Analogously to Example 17, 100 mg of the methyl ester prepared according to Example 16 yields 70 mg of the title compound as an oil.

IR: 3600, 3400 (broad), 2958, 2850, 1710, 976 cm$^{-1}$.

EXAMPLE 33

(13E)-(9R,11R,15R)-9-Fluoro-1,11,15-trihydroxy-16-phenoxy-17,18,19,20-tetranor-13-prostene At 0° C. and under agitation, 300 mg of lithium aluminum hydride is added in incremental portions to a solution of 200 mg of (13E)-(9R,11R,15R)-11,15-dihydroxy-9-fluoro-16-phenoxy-17,18,19,20-tetranor-13-prostenoic acid methyl ester (prepared according to Example 3) in 10 ml of tetrahydrofuran; the mixture is then stirred for 30 minutes at 25° C. The excess reagent is destroyed by adding ethyl acetate dropwise at 0° C., then 2 ml of water and 60 ml of ether are added and the mixture thoroughly stirred at 25° C. for 3 hours, whereafter it is filtered and the residue is washed with ether. The ether solution is dried over magnesium sulfate and evaporated under vacuum. After chromatography of the residue on silica gel with ethyl acetate/hexane (4+1), 150 mg of the title compound is obtained as an oil.

IR: 3600, 3420 (broad), 2942, 2860, 1600, 1588, 498, 976 cm$^{-1}$.

EXAMPLE 34

(13E)-(9S,11R,15R)-9-Fluoro-1,11,15-trihydroxy-16-phenoxy-17,18,19,20-tetranor-13-prostene Analogously to Example 33, 200 mg of (13E)-(9S,11R,15R)-11,15-dihydroxy-9-fluoro-16-phenoxy-17,18,19,20-tetranor-13-prostenoic acid methyl ester (prepared according to Example 4) yields 160 mg of the title compound as an oil.

IR: 3600, 3420 (broad), 2948, 2860, 1600, 1588, 1495, 975 cm$^{-1}$.

EXAMPLE 35

(5Z,13E)-(9R,11R,15R)-16,16-Dimethyl-9-fluoro-1,11,15-trihydroxy-5,13-prostadiene In analogy to Example 33, 100 mg of (5Z,13E)-(9R,11R,15R) - 11,15-dihydroxy-16,16-dimethyl-9-fluoro-5,13-prostadienoic acid methyl ester (prepared according to Example 5) yields 70 mg of the title compound as an oil.

IR: 3600, 3410 (broad), 2952, 2858, 978 cm$^{-1}$.

EXAMPLE 36

(13E)-(9R,11R,16RS)-16,19-Dimethyl-9-fluoro-1,11,15α-trihydroxy-13,18-prostadiene Analogously to Example 33, 100 mg of (13E)-(9R,11R,16RS)-11,15α-dihydroxy-16,19-dimethyl-9-fluoro-13,18-prostadienoic acid methyl ester (prepared according to Example 14) yields 72 mg of the title compound as an oil.

IR: 3600, 3420 (broad), 2962, 2840, 974 cm$^{-1}$.

EXAMPLE 37

(13E)-(9R,11R,15R)-11,15-Dihydroxy-9-fluoro-16-phenoxy-17,18,19,20-tetranor-13-prostenoic Acid Methylsulfonamide At 0° C., 90 mg of isobutyl chloroformate and 70 mg of triethylamine are added to a solution of 200 mg of (13E)-(9R,11R,15R)-11,15-dihydroxy-9-fluoro-16-phenoxy17,18,19,20-tetranor-13-prostenoic acid (prepared according to Example 19) in 5 ml of dimethylformamide. After 30 minutes, 300 mg of the sodium salt of methylsulfonamide (prepared from methylsulfonamide and sodium methylate) and 2 ml of hexamethylphosphoric triamide are added to the mixture and the latter stirred for 5 hours at 20° C. Then the mixture is diluted with citrate buffer (pH 4), extracted with ethyl acetate, the extract washed with brine, dried over magnesium sulfate, and evaporated under vacuum. Chromatography of the residue on silica gel with methylene chloride yields 150 mg of the title compound as an oil.

IR: 3600, 3405, 2950, 2856, 1718, 1600, 1588, 978 cm$^{-1}$.

EXAMPLE 38

(13E)-(9S,11R,15R)-11,15-Dihydroxy-9-fluoro-16-phenoxy-17,18,19,20-tetranor-13-prostenoic Acid Methylsulfonamide In analogy to Example 37, 100 mg of (13E)-(9S,11R,15R)-11,15-dihydroxy-9-fluoro-16-phenoxy-17,18,19,20-tetranor-13-prostenoic acid (prepared according to Example 20) yields 60 mg of the title compound as an oil.

IR: 3600, 3410, 2950, 2856, 1720, 1600, 1588, 978 cm$^{-1}$.

EXAMPLE 39

(13E)-(9R,11R,16RS)-11,15α-Dihydroxy-16,19-dimethyl-9-fluoro-13,18-prostadienoic Acid Methylsulfonamide Analogously to Example 37, 100 mg of (13E)-(9R,11R,16RS)-11,15α-dihydroxy-16,19-dimethyl-9-fluoro-13,18-prostadienoic acid (prepared according to Example 30) yields 65 mg of the title compound as an oil.

IR: 3600, 3420, 2958, 2852, 1720, 1480, 976 cm$^{-1}$.

EXAMPLE 40

(13E)-(9R,11R,15R)-11,15-Dihydroxy-9-fluoro-16-phenoxy-17,18,19,20-tetranor-13-prostenoic Acid Isopropylsulfonamide In analogy to Example 37, but using the sodium salt of isopropylsulfonamide instead of the sodium salt of methylsulfonamide, 150 mg of (13E)-(9R,11R,15R)-11,15-dihydroxy-9-fluoro-16-phenoxy-17,18,19,20-tetranor-13-prostenoic acid (prepared according to Example 19) yields 105 mg of the title compound as an oil.

IR: 3600, 3410, 2955, 2848, 1717, 1600, 1588, 976 cm$^{-1}$.

EXAMPLE 41

(13E)-(9R,11R,15R)-11,15-Dihydroxy-9-fluoro-16-phenoxy-17,18,19,20-tetranor-13-prostenoic Acid Acetylamide A solution of 600 mg of (13E)-(9R,11R,15R)-11,15-bis(tetrahydropyran-2-yloxy)-9-fluoro-16-phenoxy-17,18,19,20-tetranor-13-prostenoic acid methyl ester (produced according to Example 3) in 10 ml of methanol is stirred under argon with 2.5 ml of 2N sodium hydroxide solution for 5 hours. The mixture is concentrated under vacuum, diluted with brine, acidified with citric acid to pH 4.5, and repeatedly extracted with ethyl acetate. The organic extract is washed with brine, dried over magnesium sulfate, and evaporated under vacuum, thus obtaining as the residue 560 mg of (13E)-(9R,11R,15R)-11,15-bis(tetrahydropyran-2-yloxy)-9-fluoro-16-phenoxy-17,18,19,20-tetranor-13-prostenoic acid. To form the acetylamide, the acid is dissolved in 15 ml of acetonitrile, combined with 135 mg of triethylamine, and at 0° C. a solution of 106 mg of acetylisocyanate in 10 ml of acetonitrile is added dropwise thereto. After 2 hours at 20° C., the mixture is diluted with citrate buffer (pH 4), extracted with ether, the extract washed with brine, dried over magnesium sulfate, and evaporated under vacuum. To split off the blocking groups, the residue is stirred for 4 hours at 40° C. with 15 ml of glacial acetic acid/water/tetrahydrofuran (65/35/10) and then evaporated under vacuum. The residue is chromatographed on silica gel with methylene chloride with the addition of 0.2–1% isopropyl alcohol, thus obtaining 250 mg of the title compound as an oil.

IR: 3600, 3410, 2952, 2858, 1712, 1600, 1588, 976 cm$^{-1}$.

EXAMPLE 42

(13E)-(9R,11R,15R)-11,15-Dihydroxy-9-fluoro-16-phenoxy-17,18,19,20-tetranor-13-prostenoic Acid Amide A solution of 200 mg of (13E)-(9R,11R,15R)-11,15-dihydroxy-9-fluoro-16-phenoxy-17,18,19,20-tetranor-13prostenoic acid (prepared according to Example 19) in 5 ml of tetrahydrofuran is combined with 80 mg of isobutyl chloroformate and 60 mg of triethylamine and stirred for one hour at 0° C.; then, at 0° C., gaseous ammonia is introduced for 15 minutes and the mixture allowed to stand for one hour at 25° C. Subsequently the mixture is diluted with water, repeatedly extracted with methylene chloride, the combined extracts are washed with brine, dried over magnesium sulfate, and evaporated under vacuum. For purifying, the product is chromatographed on silica gel with methylene chloride/0.2–1% isopropyl alcohol, thus obtaining 145 mg of the title compound as an oil.

IR: 3600, 3505, 3410, 2955, 2848, 1670, 1605, 1590, 978 cm$^{-1}$.

EXAMPLE 43

(5Z,13E)-(9R,11R,15R)-11,15-Dihydroxy-9-fluoro-16-phenoxy-17,18,19,20-tetranor-5,13-prostadienoic Acid Tris(hydroxymethyl)aminomethane Salt At 65° C., a solution of 60 mg of tris(hydroxymethyl)aminomethane in 0.2 ml of water is added to a solution of 200 mg of (5Z,13E)-(9R,11R,15R)-11,15-dihydroxy-9-fluoro-16-phenoxy-17,18,19,20-tetranor-5,13-prostadienoic acid (prepared according to Example 17) in 35 ml of acetonitrile. Under agitation, the mixture is allowed to cool to 20° C., decanted off the solvent, and the residue dried under vacuum, yielding 180 mg of the title compound as a viscous oil.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A (9-Fluoroprostane derivative of the formula

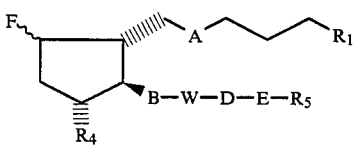

wherein
$R_1$ is $CH_2OH$ or

wherein $R_2$ is (a) hydrogen, (b) $C_{1-10}$ alkyl, (c) $C_{1-10}$ alkyl substituted by halogen; $C_{1-4}$ alkoxy; $C_{6-10}$-aryl or aroyl $C_{6-10}$-aryl or aroyl each substituted by 1-3 halogen atoms, a phenyl group, 1-3 $C_{1-4}$ alkyl groups or a chloromethyl, fluoromethyl, trifluoromethyyl, carboxy, hydroxy or $C_{1-4}$ alkoxy group; di- $C_{1-4}$-alkylamino; or tri-$C_{1-4}$-alkylammonium; (d) $C_{3-10}$-cycloalkyl, (e) $C_{3-10}$ cycloalkyl substituted by $C_{14}$ alkyl, (f) $C_{6-10}$ aryl, (g) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group or (h) an aromatic heterocycle of 5 or 6 ring atoms, one or two of which are O, N or S, the remainder being carbon atoms;
or $R_1$ is

wherein $R_3$ is an acyl group of a hydrocarbon $C_{1-15}$ carboxylic or sulfonic acid or is one of the $R_2$ groups;
A is $-CH_2-CH_2-$ or cis$-CH=CH-$;
B is $-CH_2-CH_2-$, trans$-CH=CH-$ or $C\equiv C-$;
W is hydroxymethylene or RO-methylene, wherein the OR or OH group is in a α- or β-position;
R is tetrahydrophyranyl, tetrahydrofuranyl, α-ethoxyethyl, trimethylsilyl, dimethyl-tert-butylsilyl, tribenzylsilyl or an acyl group of a $C_{1-15}$-hydrocarbon carboxylic or sulfonic acid;
D and E jointly are a direct bond or
D is straight-chain or branched alkylene or alkenylene of 1-10 carbon atomns, optionally substituted by 1-2 fluorine atoms and E is a direct bond, or
$-CR_6=CR_7-$ wherein $R_6$ and $R_7$ differ from each other and each is hydrogen, chlorine or $C_{1-6}$-alkyl;
$R_4$ is OH or OR;
$R_5$ is (a) hydrogen, (b) a $C_{1-10}$ hydrocarbon aliphatic radical, or (c) a $C_{6-10}$ hydrocarbon aliphatic radical substituted by halogen,
or when $R_2$ is hydrogen a physiologically compatible salt thereof with a base,
and wherein the 16-position (prostanosic acid nomenclate) is substituted by an alkyl group.

2. (5Z,13E)-(9R,11R,15R)-11,15-Dihydroxy-16,16-dimethyl-9-fluoro-5,13-prostadienoic acid methyl ester, a compound of claim 1.

3. (5Z,13E)-(9S,11R,15R)-11,15-Dihydroxy-16,16-dimethyl-9-fluoro-5,13-prostadienoic acid methyl ester, a compound of claim 1.

4. (13E)-(9R,11R,15R)-11,15-Dihydroxy-16,16-dimethyl-9-fluoro-13-prostenoic acid methyl ester, a compound of claim 1.

5. (5Z,13E)-(9R,11R,16RS)-11,15α-Dihydroxy-9-fluoro-16-methyl-5,13-prostadienoic acid methyl ester, a compound of claim 1.

6. (5Z,13E)-(9S,11R,16RS)-11,15α-Dihydroxy-9-fluoro-16-methyl-5,13-prostadienoic acid methyl ester, a compound of claim 1.

7. (5Z,13E)-(9R,11R,16RS)-11,15α-Dihydroxy-16,19-dimethyl-9-fluoro-5,13,18-prostatrienoic acid methyl ester, a compound of claim 1.

8. (5Z,13E)-(9S,11R,16RS)-11,15α-Dihydroxy-16,19-dimethyl-9-fluoro-5,13,18-prostatrienoic acid methyl ester, a compound of claim 1.

9. (13E)-(9R,11R,16RS)-11,15α-Dihydroxy-16,19-dimethyl-9-fluoro-13,18-prostadienoic acid methyl ester, a compound of claim 1.

10. (13E)-(9S,11R,16RS)-11,15α-Dihydroxy-16,19-dimethyl-9-fluoro-13,18-prostadienoic acid methyl ester, a compound of claim 1.

11. (5Z,13E)-(9R,11R,15R)-11,15-Dihydroxy-9-fluoro-16,16,19-trimethyl-5,13,18-prostatrienoic acid methyl ester, a compound of claim 1.

12. (5Z,13E)-(9R,11R,15R)-11,15-Dihydroxy-16,16-dimethyl-9-fluoro-5,13-prostadienoic acid, a compound of claim 1.

13. (5Z,13E)-(9S,11R,15R)-11,15-Dihydroxy-16,16-dimethyl-9-fluoro-5,13-prostadienoic acid, a compound of claim 1.

14. (13E)-(9R,11R,15R)-11,15-Dihydroxy-16,16-dimethyl-9-fluoro-13-prostenoic acid, a compound of claim 1.

15. (5Z,13E)-(9R,11R,16RS)-11,15α-Dihydroxy-9-fluoro-16-methyl-5,13-prostadienoic acid, a compound of claim 1.

16. (5Z,13E)-(9S,11R,16RS)-11,15α-Dihydroxy-9-fluoro-16-methyl-5,13-prostadienoic acid, a compound of claim 1.

17. (5Z,13E)-(9R,11R,16RS)-11,15α-Dihydroxy-16,19-dimethyl-9-fluoro-5,13,18-prostatrienoic acid, a compound of claim 1.

18. (5Z,13E)-(9S,11R,16RS)-11,15α-Dihydroxy-16,19-dimethyl-9-fluoro-5,13,18-prostatrienoic acid, a compound of claim 1.

19. (13E)-(9R,11R,16RS)-11,15α-Dihydroxy-16,19-dimethyl-9-fluoro-13,18-prostadienoic acid, a compound of claim 1.

20. (13E)-(9S,11R,16RS)-11,15α-Dihydroxy-16,19-dimethyl-9-fluoro-13,18-prostadienoic acid, a compound of claim 1.

21. (5Z,13E)-(9R,11R,15R)-11,15-Dihydroxy-9-fluoro-16,16,19-trimethyl-5,13,18-prostatrienoic acid, a compound of claim 1.

22. (5Z,13E)-(9R,R,15R)-16,16-Dimethyl-9-fluoro-1,11,15-trihydroxy-5,13-prostadiene, a compound of claim 1.

23. (13E)-(9R,11R,16RS)-16,19-Dimethyl-9-fluoro-1,11,15α-trihydroxy-13,18-prostadiene, a compound of claim 1.

24. (13E)-(9R,11R,16RS)-11,15α-Dihydroxy-16,19-dimethyl-9-fluoro-13,18-prostadienoic acid methylsulfonamide, a compound of claim 1.

25. A compound of claim 1 wherein A is —CH$_2$—CH$_2$—.

26. A compound of claim 1 wherein R$_1$ is CH$_2$OH.

27. A compound of claim 1 wherein R$_1$ is —CONHR$_3$.

28. A compound of claim 1 wherein R$_2$ is
    (a) C$_{1-10}$ alkyl substituted by C$_{6-10}$-aryl or aroyl; C$_{6-10}$-aryl or aroyl each substituted by 1-3 halogen atoms, a phenyl group, 1-3 C$_{1-4}$ alkyl groups or a chloromethyl, fluoromethyl, trifluoromethyl, carboxy, hydroxy or C$_{1-4}$ alkoxy group; di-C$_{1-4}$-alkylamino; or tri-C$_{1-4}$-alkylammonium;
    (b) C$_{3-10}$ cycloalkyl,
    (c) C$_{3-10}$ cycloalkyl substituted by C$_{1-4}$ alkyl,
    (d) C$_{6-10}$ aryl,
    (e) C$_{6-10}$ aryl substituted by 1-3 halogen atoms, a phenyl group, 1-3 C$_{1-4}$ alkyl groups or a chloromethyl, fluoromethyl, trifluoromethyl, carboxy, hydroxy or C$_{1-4}$ alkoxy group, or
    (f) an aromatic heterocycle of 5 or 6 ring atoms, one or two of which are O, N or S, the remainder being carbon atoms.

29. A compound of claim 1 wherein B is —C≡C—.

30. A compound of claim 1 wherein the 16-position is substituted by CH$_3$ or F.

31. A compound of claim 1 wherein the 16-position is substituted by CH$_3$.

32. A compound of claim 1 wherein R$_5$ is a C$_{1-10}$-hydrocarbon aliphatic radical substituted by halogen.

33. A compound according to claim 1, wherein the 16-position is disubstituted by methyl.

34. A compound according to claim 1, wherein the 16-position is disubstituted.

35. A compound of claim 1 wherein

B—W—D—E—R$_5$ is 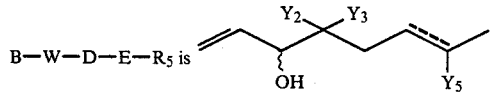

wherein each of Y$_2$, Y$_3$ or Y$_5$ independently is H or CH$_3$, and Y$_3$ can also be F; and ⌇ represents a single or double bond.

36. A pharmaceutical composition comprising an amount of a compound of claim 1 effective to trigger luteolysis and a pharmaceutically acceptable carrier.

37. A method of achieving a luteolytic effect in a patient in whom it is desired to achieve such an effect comprising administering to the patient an amount of a compound effective to trigger luteolysis, having the formula:

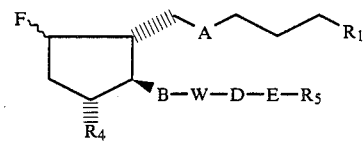

wherein
Rhd 1 is CH$_2$OH or

wherein R$_2$ is (a) hydrogen, (b) C$_{1-10}$-alkyl, (c) C$_{1-10}$ alkyl substituted by halogen; C$_{1-4}$alkoxy; C$_{6-10}$aryl or aroyl; C$_{6-10}$aryl or aroly each substituted by 1-3 halogen atoms, a phenyl group, 1-3 C$_{1-4}$ alkyl groups or a chloromethyl, fluoromethyl, trifluoromethyl, carboxy, hydroxy or C$_{1-4}$ alkoxy group; di- C$_{1-4}$-alkylamino; or tri-C$_{1-4}$-alkylammonium; (d) C$_{3-10}$-cycloalkyl, (e) C$_{3-10}$ cycloalkyl substituted by C$_{1-4}$ alkyl, (f) C$_{6-10}$ aryl, (g) C$_{6-10}$aryl substituted by 1-3 halogen atoms, a phenyl group, 1-3 C$_{1-4}$ alkyl groups or a chloromethyl, fluoromethyl, trifluoromethyl, carboxy, hydroxy or C$_{1-4}$ alkoxy group or (h) an aromatic heterocycle of 5 or 6 ring atoms, one or two of which are O, N or S, the remainder being carbon atoms;

or R$_1$ is

wherein R$_3$ is an acyl group of a hydrocarbon C$_{1-15}$ carboxylic or sulfonic acid or is one of the R$_2$ groups;

A is —CH$_2$—CH$_2$—or cis—CH=CH—;

B is —CH$_2$—CH$_2$—, trans—CH=CH—or C≡C—;

W is hydroxymethylene or RO-methylene, wherein the OR or OH group is in a α- or β-position;

R is tetrahydrophyranyl, tetrahydrofuranyl, α-ethoxyethyl, trimethylsilyl, dimethyl-tert-butylsilyl, tribenzylsilyl or an acyl group of a C$_{1-15}$-hydrocarbon carboxylic or sulfonic acid;

D and E jointly are a direct bond or

D is straight-chain or branched alkylene or alkenylene of 1-10 carbon atoms, optionally substituted by 1-2 fluorine atoms and E is a direct bond, or —CR$_6$—CR$_7$—wherein R$_6$ and R$_7$ differ from each other and each is hydrogen, chlorione or R$_4$ is OH or;

R$_5$ is (a) hydrogen, (b) a C$_{1-10}$ hydrocarbon aliphatic radical, or (c) a C$_{6-10}$ hydrocarbon aliphatic radical substituted by halogen, or when R$_2$ is hydrogen a physiologically compatible salt thereof with a base.

38. A pharmaceutical composition comprising an amount of a compound of claim 1 effective to reduce sweling of nasal mucous membranes and a pharmaceutically-acceptable carrier.

39. A method of reducing the swelling of nasal mucous membranes in a patient in need of such treatment comprising administering to the patient an amount of a compound of claim 1 effective to reduce the swelling of nasal mucous membranes.

* * * * *